(12) United States Patent
Smith, Jr. et al.

(10) Patent No.: US 8,153,854 B2
(45) Date of Patent: Apr. 10, 2012

(54) GASOLINE ALKYLATE RVP CONTROL

(75) Inventors: Lawrence A. Smith, Jr., Pasadena, TX (US); Abraham P. Gelbein, Raleigh, NC (US); William M. Cross, Jr., Seabrook, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 921 days.

(21) Appl. No.: 12/134,652

(22) Filed: Jun. 6, 2008

(65) Prior Publication Data

US 2009/0306448 A1    Dec. 10, 2009

(51) Int. Cl.
*C07C 2/02* (2006.01)

(52) U.S. Cl. ........ 585/520; 585/251; 585/332; 585/529; 585/712; 585/719; 585/721; 585/730

(58) Field of Classification Search .......... 585/251, 585/332, 520, 529, 712, 719, 720, 721, 730
See application file for complete search history.

(56) References Cited

U.S. PATENT DOCUMENTS

| | | | |
|---|---|---|---|
| 2,375,867 A * | 5/1945 | Newman | 585/251 |
| 2,762,853 A | 9/1956 | Jones et al. | |
| 2,859,260 A | 11/1958 | Stiles | |
| 3,013,092 A | 12/1961 | Watson et al. | |
| 4,242,530 A | 12/1980 | Smith, Jr. | |
| 4,313,016 A | 1/1982 | Manning | |
| 4,375,576 A | 3/1983 | Smith, Jr. | |
| 4,540,839 A | 9/1985 | Keyworth et al. | |
| 4,695,664 A | 9/1987 | Whittle | |
| 4,956,514 A | 9/1990 | Chu | |
| 5,003,124 A | 3/1991 | Smith, Jr. et al. | |
| 5,510,555 A | 4/1996 | Brunelli et al. | |
| 5,583,275 A | 12/1996 | Kranz et al. | |
| 5,659,096 A * | 8/1997 | Randolph et al. | 585/332 |
| 5,730,843 A | 3/1998 | Groten et al. | |
| 6,000,685 A | 12/1999 | Groten et al. | |
| 6,143,942 A | 11/2000 | Verrelst et al. | |
| 6,335,473 B1 | 1/2002 | Bakshi et al. | |
| 6,429,349 B1 | 8/2002 | Grimes et al. | |
| 6,501,001 B2 | 12/2002 | Commereuc et al. | |
| 6,995,296 B2 | 2/2006 | Smith, Jr. et al. | |
| 2004/0260136 A1 * | 12/2004 | Smith et al. | 585/730 |

* cited by examiner

*Primary Examiner* — Prem C Singh
(74) *Attorney, Agent, or Firm* — Osha • Liang LLP

(57) ABSTRACT

A process for producing an alkylate having a low Reid vapor pressure, the process including: contacting a $C_{6+}$-containing hydrocarbon stream with a mixture of isopentane and isobutane in the presence of an acid catalyst in an alkylation reactor to form a dilute alkylate product, wherein the $C_{6+}$-containing hydrocarbon stream includes at least one of oligomers of $C_3$ to $C_5$ olefins and a dilute alkylate produced by contacting an isoparaffin with at least one of $C_3$ to $C_5$ olefins and oligomers of $C_3$ to $C_5$ olefins; fractionating the dilute alkylate product to form an isobutane-rich fraction, a n-butane-rich fraction, a fraction containing isopentane, and an alkylate product having a Reid vapor pressure less than 0.35 bar (5 psi); recycling at least a portion of the fraction containing isopentane to the alkylation reactor.

21 Claims, 3 Drawing Sheets

GASOLINE ALKYLATE RVP CONTROL

BACKGROUND OF DISCLOSURE

1. Field of the Disclosure

Embodiments disclosed herein relate generally to the alkylation of paraffinic hydrocarbon feedstocks wherein olefins are reacted with isobutane and isopentane to produce a low Reid vapor pressure alkylate product.

2. Background

Alkylation is the reaction of a paraffin, usually isoparaffins, with an olefin in the presence of a strong acid which produces paraffins, e.g., of higher octane number than the starting materials and which boil in the range of gasolines. In petroleum refining, the reaction is generally the reaction of a $C_3$ to $C_5$ olefin with isobutane.

Hydrofluoric or sulfuric acid catalysts are commonly used in refining alkylations. For sulfuric acid catalyzed alkylation, low temperature or cold acid processes are favored, minimizing side reactions. In a typical process, the alkylation is carried out in a reactor where the hydrocarbon reactants are dispersed into a continuous acid phase.

For example, U.S. Pat. No. 2,762,853 discloses an alkylation process including feeding isoparaffins, such as isobutane or isopentane and $C_2$-$C_5$ monoolefins to an alkylation reactor. The alkylation reaction is catalyzed with sulfuric acid in excess of 88 percent, preferably in excess of 96 percent $H_2SO_4$. The alkylation products are then separated into gasoline range components and heavier alkylate products, among other finishing processes. Other alkylation processes are disclosed in, for example, U.S. Pat. Nos. 2,859,260 and 3,013,092.

U.S. Pat. No. 6,995,296 discloses a process for the alkylation of alkane with olefin or olefin precursor such as an oligomer of tertiary olefin. The alkylation may be performed by contacting an acid catalyst, isoparaffin and olefin in concurrent downflow with a disperser mesh in a reaction zone under conditions of temperature and pressure to react the isoparaffin and the olefin to produce an alkylate product. The olefin precursor may include an oligomer comprising $C_8$ to $C_{16}$ olefins corresponding to oligomers prepared from $C_3$ to $C_5$ olefins. Instead of the expected reaction between the oligomer and the isoalkane, the oligomer is split into its olefin constituents that react with the isoalkane on a molar basis.

Recent reformulated gasoline specifications require a reduction in both the olefin content and the Reid Vapor Pressure (RVP) of the gasoline. Alkylate is a low vapor pressure, high octane gasoline blending component containing no olefins. Thus, alkylate helps refiners meet the new reduced RVP and reduced olefins content specifications.

As practiced commercially, alkylate product resulting from the reaction of $C_3$ to $C_5$ olefins with isobutane is typically $C_7$ to $C_9$ isoparaffins, along with lesser amounts of lighter and heavier isoparaffins in the $C_6$ to $C_{12}$ range. Isopentane is also produced during the alkylation reaction. The production of isopentane during alkylation of isobutane may increase isopentane concentration in the final gasoline pool, and, with an RVP of 20.5 psi, negatively affects the desired or targeted RVP and resultant yield.

Alkylation of isopentane is one method to reduce its RVP. However, alkylation of pure isopentane or suppression of isopentane products from amylene alkylation results in low $C_{5+}$ yields, lower octane value products relative to isobutane alkylates, and low isopentane conversions.

U.S. Pat. No. 5,583,275 discloses an alkylation process in which $C_3$ to $C_5$ olefins are reacted with an isoparaffin mixture of isopentane and isobutane in the presence of a catalyst. As disclosed therein, varying the amount of isopentane present in the isoparaffin mixture can control or eliminate the amount of isopentane produced in the alkylation reactor, and may produce an alkylate having a lower RVP and may result in a lower olefin content for reformulated gasoline.

U.S. Pat. No. 6,429,349 discloses an alkylation process in which low purity isopentane is added to an alkylation reactor to block formation of isopentane, which may result in high incremental isopentane conversion and minimal octane and $C_{5+}$ yield loss, as well as low acid consumption from $C_{6+}$ isoparaffins.

Accordingly, there exists a need for alkylation processes that may provide for reduced olefin content in reformulated gasoline and allow for a decrease in RVP.

SUMMARY OF THE DISCLOSURE

In one aspect, embodiments disclosed herein relate to a process for producing an alkylate having a low Reid vapor pressure, the process including: contacting a $C_{6+}$-containing hydrocarbon stream with a mixture of isopentane and isobutane in the presence of an acid catalyst in an alkylation reactor to form a dilute alkylate product, wherein the $C_{6+}$-containing hydrocarbon stream includes at least one of oligomers of $C_3$ to $C_5$ olefins and a dilute alkylate produced by contacting an isoparaffin with at least one of $C_3$ to $C_5$ olefins and oligomers of $C_3$ to $C_5$ olefins; fractionating the dilute alkylate product to form an isobutane-rich fraction, a n-butane-rich fraction, a fraction containing isopentane, and an alkylate product having a Reid vapor pressure less than 0.35 bar (5 psi); recycling at least a portion of the fraction containing isopentane to the alkylation reactor.

In another aspect, embodiments disclosed herein relate to a process for producing an alkylate having a relatively low Reid vapor pressure, the process including: contacting a first hydrocarbon stream including at least one of $C_3$ to $C_5$ olefins and oligomers of $C_3$ to $C_5$ olefins with isobutane in the presence of an acid catalyst in a first alkylation reactor to form a dilute alkylate of $C_3$ to $C_5$ olefins; contacting the dilute alkylate of $C_3$ to $C_5$ olefins and a second hydrocarbon stream including at least one of $C_3$ to $C_5$ olefins and oligomers of $C_3$ to $C_5$ olefins with isopentane in a second alkylation reactor to form a second dilute alkylate of $C_3$ to $C_5$ olefins; fractionating the second dilute alkylate to form an isobutane-rich fraction, a n-butane-rich fraction, a fraction containing isopentane, and an alkylate product having a Reid vapor pressure less than 0.35 bar (5 psi); recycling at least a portion of the fraction containing isopentane to the second alkylation reactor; and recycling at least a portion of the isobutane-rich fraction to the first alkylation reactor.

In another aspect, embodiments disclosed herein relate to a process for producing an alkylate having a relatively low Reid vapor pressure, the process including: oligomerizing $C_3$ to $C_5$ olefins to form oligomers of $C_3$ to $C_5$ olefins; contacting the oligomers of $C_3$ to $C_5$ olefins with at least one of isopentane and isobutane in the presence of an acid catalyst in an alkylation reactor to form a dilute alkylate; fractionating the dilute alkylate to form an isobutane-rich fraction, a n-butane-rich fraction, a fraction containing isopentane, and an alkylate product having a Reid vapor pressure less than 0.35 bar (5 psi); recycling at least a portion of the fraction containing isopentane to the alkylation reactor.

Other aspects and advantages will be apparent from the following description and the appended claims.

DETAILED DESCRIPTION

Figure 1:
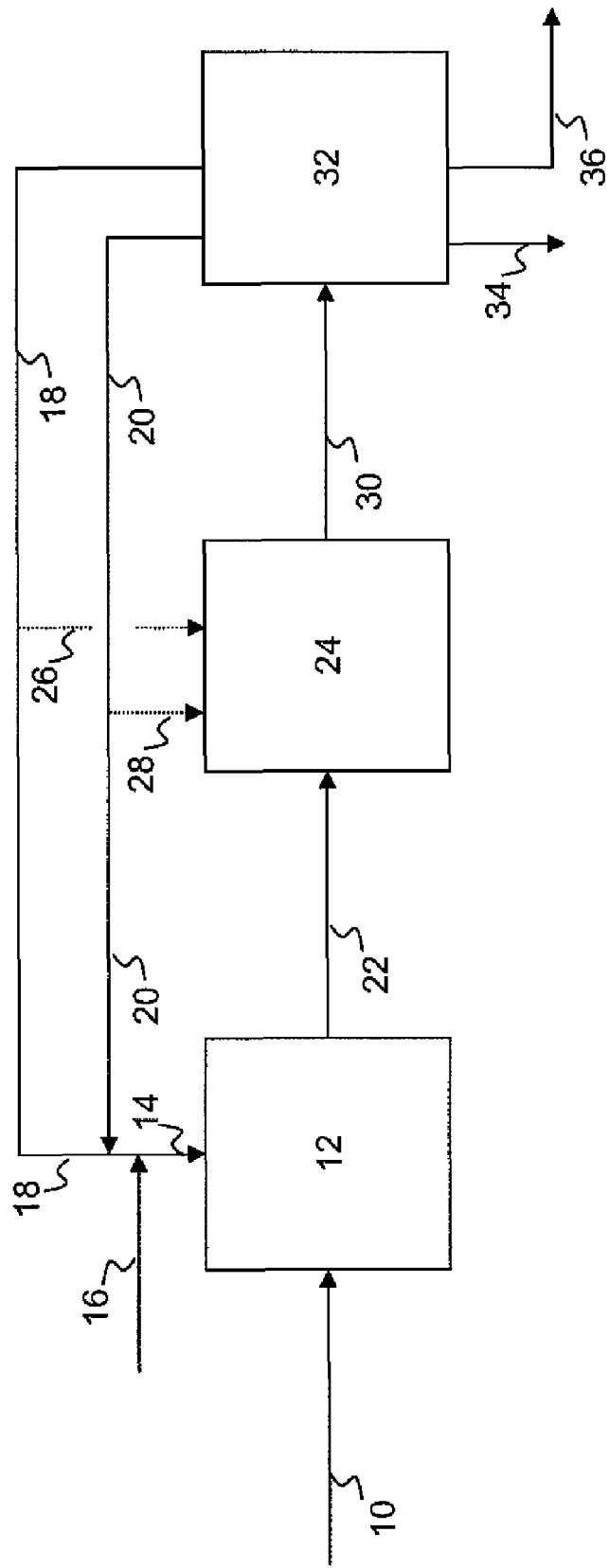
FIG. 1 is a simplified flow diagram of alkylation processes according to embodiments disclosed herein.

In one aspect, embodiments disclosed herein relate to the alkylation of paraffinic hydrocarbon feedstocks wherein olefins are reacted with isobutane and isopentane to form an alkylate product. In other aspects, embodiments disclosed herein relate to the alkylation of isobutane and isopentane to produce a low Reid vapor pressure alkylate, separation of the isopentane from the alkylate product, and recycle of isopentane to the alkylation reactor.

In general, embodiments disclosed herein relate to processes for producing an alkylate having a low Reid vapor pressure. The processes may include contacting a $C_{6+}$-containing hydrocarbon stream and a mixture of isopentane and isobutane in the presence of an acid catalyst in an alkylation reactor to form a dilute alkylate. The $C_{6+}$-containing hydrocarbon stream may include at least one of a) oligomers of $C_3$ to $C_5$ olefins, and b) a dilute alkylate of $C_3$ to $C_5$ isoparaffins with at least one of $C_3$ to $C_5$ olefins and oligomers of $C_3$ to $C_6$ olefins. The resulting dilute alkylate may be fractionated to form an isobutane-rich fraction, a n-butane-rich fraction, a fraction comprising isopentane, and an alkylate product having a Reid vapor pressure less than 0.35 bar (5 psi); in other embodiments, the Reid vapor pressure may be less than 0.28 bar (4 psi); and less than 0.21 bar (3 psi) in yet other embodiments. The isobutane and isopentane fractions may be recycled to the alkylation reactor, where the isopentane recycle may aid in controlling the formation or production of isopentane during the alkylation process, allowing a reduction in product RVP.

Processes described herein relate to alkylation of isoparaffins and olefins, where the hydrocarbon feed to the alkylation unit includes at least one of $C_{6+}$ olefins and $C_{6+}$ isoparaffins. One of ordinary skill in the art would expect that these $C_{6+}$ feeds would result in undesired alkylate products and poor product quality. For example, higher molecular weight olefins are generally considered to form high molecular weight alkylate. Additionally, feeding $C_{6+}$ isoparaffins to an alkylation reactor, particularly $C_8$ isoparaffins, is considered to decrease product quality. However, the inventors of the processes disclosed herein have found that use of these $C_{6+}$ olefin and isoparaffin feeds, when used with isopentane recycle, may control or reduce the formation or production of isopentane during the alkylation process. Due to the decreased isopentane production, an alkylate product having improved RVP may be produced, without a decrease in product quality. Additionally, this low Reid vapor pressure alkylate may be produced without significant formation of undesired heavy hydrocarbon products (i.e., $C_{13}$ to $C_{24}$ hydrocarbons).

Olefins

In some embodiments of the alkylation processes described herein, olefins are reacted with isoparaffins. Olefins used may include $C_3$ to $C_5$ olefins in some embodiments. In other embodiments, olefins may include dimers and trimers of the $C_3$ to $C_5$ olefins, such as may be formed in an olefin oligomerization process.

Olefin Oligomerization

In some embodiments of the alkylation processes described herein, $C_{6+}$-containing hydrocarbon streams may include oligomers of $C_3$ to $C_5$ olefins, as mentioned above. Preferably, the oligomer comprises $C_6$ to $C_{16}$ olefins corresponding to oligomers prepared from $C_3$ to $C_5$ olefins. In a preferred embodiment the oligomers have 6 to 16 carbon atoms and correspond to oligomers which are prepared from $C_4$ to $C_5$ olefins. The oligomerization of the tertiary olefin is also a preferred reaction when carried out on a light naphtha stream with the separation of normal olefin being easily achieved by fractionation from the heavier (higher boiling) oligomers (mainly dimers and trimers). The oligomers may be used as gasoline components but there are limits to the amount of olefin material desirable or allowed in gasoline and it is frequently necessary to hydrogenate the oligomers for use in gasoline. The most desirable component among these hydrogenated oligomers for gasoline blending is $C_8$, e.g., isooctane (2,2,4-trimethyl pentane).

When the oligomerization is carried out in a catalytic distillation type reaction, the heat of reaction is removed as boil-up, where the material subject to boil-up, in this type of reaction, is the lower boiling mono-olefins and alkanes which are being separated from the oligomer. Thus, even though there is heat produced in the oligomerization, it is of no cost to the production of the gasoline, since the heat is used in the fractionation, and the operating cost of the alkylation unit is reduced by the use of oligomer to replace some or all of the conventional short chain olefin.

The oligomerization of isoolefins may be carried out in a partial liquid phase in the presence of an acid cation resin catalyst either in straight pass type reaction or in a catalytic distillation reaction where there is both a vapor and liquid phase and a concurrent reaction/fractionation. Catalysts used in oligomerization reactors may include acid resins, such as AMBERLYST 15 or related oleum derived resins and may include phosphoric acid derived catalysts, such as those known to the industry as SPA (solid phosphoric acid) catalysts.

The feed to the oligomerization reactor may include a $C_4$-$C_5$, $C_4$ or $C_5$ light naphtha cut. The tertiary olefins may include isobutene and isoamylenes, which are more reactive than the normal olefin isomers and are preferentially oligomerized. The primary oligomerization products are dimers and trimers of the $C_3$ to $C_5$ olefins. The isoalkanes in the $C_4$ to $C_5$ light naphtha cut may include isobutane, isopentane or mixtures thereof, as a diluent in the oligomerization reactor. When a straight pass oligomerization reactor is used, such as that disclosed in U.S. Pat. Nos. 4,313,016; 4,540,839; 5,003,124; and 6,335,473, the entire effluent comprising the oligomer, normal olefins and isoalkanes may be fed to an acid alkylation reaction. Additional isobutane may be fed to the oligomerization reactor to provide additional heat sink to remove a portion of the heat of reaction.

The $C_4$ to $C_5$ light naphtha cut may also include normal alkanes. The normal alkanes are inert under the conditions of the present alkylation. Under alkylation conditions the isoalkane reacts with the olefins to form alkylate product and with the individual constituent olefins of the oligomers (i.e., the olefins may correspond to those used in the oligomerization) to form the alkylate product. The result of the present process is that the oligomers are dissociated or in some manner make their constituent olefins available for reaction with isoalkanes. Thus, the reaction will produce: 1) isobutene oligomer+isobutane→isooctane; 2) isobutene oligomer+isopentane→branched $C_9$ alkanes; 3) isoamylene oligomer+isobutane→branched $C_9$ alkanes; 4) isoamylene oligomer+isopentane→branched $C_{10}$ alkanes; whereas it would have been expected that reaction 1) would produce at least or mostly $C_{12}$ alkanes, reaction 2) would produce at least or mostly $C_{13}$ alkanes, reaction 3) would produce at least or mostly $C_{14}$ alkanes, and reaction 4) would produce at least or mostly $C_{15}$ alkanes.

When a catalytic distillation reaction such as that disclosed in U.S. Pat. Nos. 4,242,530 or 4,375,576 is used for the oligomerization, the oligomer is separated from the lower boiling normal olefins and alkanes in the reaction product by concurrent fractionation. The streams, normal olefins and alkanes (overheads) and oligomers (bottoms), may be united or individually fed to the alkylation or may be used individually with at least the oligomer being fed to the alkylation.

The oligomerization of propylene may be carried out in tubular reactors at 330-482° F. and 1000 to 1215 psig using supported phosphoric acid (sPa), metal complexes (U.S. Pat. Nos. 5,510,555; 4,695,664 and 6,501,001) and various zeolites, especially ZSM-22, ZSM-57 (U.S. Pat. No. 6,143,942) and MCM-22 (U.S. Pat. No. 4,956,514) which has been shown to have favorable characteristics for the oligomerization of propylene at lower pressures and temperatures than the other catalysts.

The reaction of oligomer of tertiary olefins with isoalkanes is on a molar basis with the tertiary olefins of the oligomer, rather than with the oligomers. The alkylate product corresponds to the reaction of the tertiary olefin and isoalkanes. For the purpose of illustration and not a limitation of the process, it is believed that instead of the expected reaction between the oligomer and the isoalkane, the oligomer is cracked into olefin components which react with the isoalkane on a molar basis:

1) diisobutene+2 isobutane→2 isooctane (2,2,4-trimethyl pentane)
2) triisobutene+3 isobutane→3 isooctane (2,2,4-trimethyl pentane)

The conventional view in the art had been that the product of 1) would be a $C_{12}$ alkane and the product of 2) would be a $C_{16}$ alkane, whereas it has been found that the product of reactions 1) and 2) is the same component, and is indistinguishable from a conventional cold acid alkylation product of the reaction:

3) 2 butene-2+2 isobutane→2 isooctane
4) 3 butene-2+3 isobutane→3 isooctane

As mentioned previously, acid alkylation reactions are highly exothermic, requiring substantial refrigeration to maintain the reaction temperature in the desired range and to prevent undesired side reactions. One advantage of alkylation with oligomers is that the reaction of the oligomers with the isoalkane to produce alkylate in the same yields requires less refrigeration, making the process less expensive for the same yield of useful product.

The oligomer may be cracked back to the original olefins and used in cold acid reaction; however, it is not necessary to crack the oligomer which may constitute the olefin feed to cold acid reaction with the isoalkane. As noted above, the result of feeding the oligomers is the same or better product as if the mono-olefin, per se, were fed to the alkylation, with the additional benefit of a less exothermic overall alkylation reaction requiring less refrigeration and, hence, a lower energy cost for the alkylation.

Alkylation

In embodiments of the alkylation processes disclosed herein, a mixture of isoparaffins is reacted with olefins in the presence of an alkylation catalyst to form high-octane gasoline components. The precise process steps and process conditions may vary depending upon the catalyst system used. It is anticipated that any suitable catalyst may be used, including liquid, solid, or any other type of catalyst.

In the practice of the alkylation processes disclosed herein, the reacting hydrocarbons may include $C_3$ to $C_5$ olefins, oligomers of $C_3$ to $C_5$ olefins, as well as $C_4$ and $C_5$ isoparaffins, or mixtures thereof. In some embodiments, the feed to the alkylation processes disclosed herein may also include $C_{6+}$ isoparaffins, such as $C_8$ and $C_9$ isoparaffins produced in a previous alkylation stage. The composition of the olefins and isoparaffins fed to the alkylation process may be used to control the amount and type of isoparaffins produced in the alkylation, and in some embodiments the composition of the isoparaffins may be manipulated by recycling various isoparaffins, including isopentanes, to the alkylation reactor(s). Recycle of isopentanes has been found to decrease the production or formation of isopentanes during the alkylation processes disclosed herein, thus decreasing the net amount of isopentanes in the alkylate product.

The alkylation processes disclosed herein are typically operated with ratios of isoparaffin to olefin in the feed streams to the reactors of greater than 1 to minimize undesired polymerization reactions. The isoparaffin to olefin ratio may be generally in the range from about 2:1 to about 50:1; from about 4:1 to about 20:1 in other embodiments; and from about 10:1 to about 15:1 in yet other embodiments. For sulfuric acid catalyzed alkylations, the isoparaffin to olefin ratio may be in the range from about 5:1 to about 10:1.

Olefins may be fed to the reactor as oligomers in various embodiments disclosed herein. In some embodiments, the oligomers may include dimers and trimers of $C_3$ to $C_5$ olefins. In other embodiments, the oligomers may be primarily dimers of $C_3$ to $C_5$ olefins. Feed streams with oligomerized olefins may be fed at ratios of isoparaffin to oligomerized olefins at a ratio of greater than 0.5:1 in some embodiments; greater than 1:1 in other embodiments; greater than 1.5:1 in other embodiments; and greater than 2:1 in yet other embodiments.

The alkylation may be carried out by contacting an alkylation catalyst, described below, and the reacting hydrocarbons in a reactor under controlled conditions (temperature, pressure, etc.). Alkylation reactions are very exothermic and may require cooling to remove the heat of reaction from the reactor.

Alkylation reactor systems useful in embodiments of the processes disclosed herein include time-tank or pipe reactors, cascade reactors, gravity reactors, trickle bed reactors, solid catalyst reactors, and the like, where the reactors may be co-current or counter-current reactors. Other reactors that may be useful include boiling point reactors, down flow boiling point reactors, pulse flow reactors, and the like. In some embodiments, the reactor may be operated with a hydrocarbon-continuous phase (dispersed acid phase). In other embodiments, the reactor may be operated with an acid-continuous phase (dispersed hydrocarbon phase).

The alkylation catalyst used may be any catalyst that will catalytically effect the reaction of the paraffins and olefins. Suitable catalysts include strong acid catalysts, such as hydrofluoric acid, sulfuric acid, phosphoric acid, mixtures of sulfuric and phosphoric acids, metal halides such as aluminum chloride and aluminum bromide, complexes of aluminum chloride and sulfuric acid, and the like. Suitable solid alkylation catalysts may include macroreticular acid ion exchange resins in the presence of boron trifluoride, zeolite catalysts, acid washed silica treated with antimony pentafluoride, and others as may be known in the art.

Acid strength of the catalyst used is generally maintained high enough to avoid dilution of the acid catalyst but low enough to avoid excessive side reactions. For example, the range of useful strengths of sulfuric acid may be in the range from about 86 to about 99 weight percent. The volume ratio of catalyst to total hydrocarbon is generally in the range from about 10:1 to about 1:10.

The alkylation temperature and pressure used is generally selected to yield the desired alkylation products without undue detrimental effects upon the catalyst or alkylation reactants, such as catalyst deactivation, excessive side reactions, cracking, polymerization, or carbon formation. Generally, the alkylation temperature will be in the range from about −51° C. to about 93° C. (about −60° F. to about 200° F.). In other embodiments, the alkylation temperature may be in the range from about −40° C. to about 71° C. (about −40° F. to about 160° F.); from about −17° C. to about 60° C. (about 0° F. to about 140° F.) in other embodiments; and from about 2° C. to about 52° C. (about 35° F. to about 125° F.) in yet other embodiments. The alkylation pressure may range from about atmospheric pressure to about 35 bar (500 psia) in some embodiments; from about 1.7 bar (25 psia) to about 27 bar (400 psia) in other embodiments; and from about 3.5 bar (50 psi) to about 17 bar (250 psia) in yet other embodiments.

Although the residence time of the reactants in the reactor may vary widely depending upon process variables, the residence time is generally in the range from about 0.01 to about 100 minutes. In other embodiments, the residence time may be in the range from 0.1 minutes to about 30 minutes; from about 1 to about 20 minutes in other embodiments; and from about 5 to about 20 minutes in yet other embodiments.

In one embodiment of the present alkylation process, a light naphtha stream comprising normal and tertiary olefins (typically a light naphtha from a catalytic cracking unit) is contacted with an acid resin catalyst under oligomerization conditions to preferentially react a portion of the tertiary olefins with themselves to form oligomers, and feeding said oligomers to an alkylation zone with an isoalkane in the presence of an acid alkylation catalyst to produce an alkylation product comprising the alkylate of said tertiary olefin and said isoalkane.

The feed to the alkylation may include one or both isoolefin oligomers as well as propylene oligomers. Embodiments of the present processes may include an alkylation unit including a downflow reactor packed with contacting internals or packing material (which may be inert or catalytic) through which passes a concurrent multi-phase mixture of sulfuric acid, hydrocarbon solvent and reactants at the boiling point of the system. The system includes a hydrocarbon phase and an acid/hydrocarbon emulsion phase. A significant amount of sulfuric acid may be held up on the packing.

Reaction is believed to take place between the descending hydrocarbon phase and the sulfuric acid dispersed on the packing. Olefin continuously dissolves into the acid phase and alkylate product is continuously extracted into the hydrocarbon phase. Adjusting the pressure and hydrocarbon composition controls the boiling point temperature. The reactor is preferentially operated vapor-continuous but may also be operated liquid-continuous. The pressure is preferentially higher at the top of the reactor than at the bottom.

Adjusting the flow rates and the degree of vaporization controls the pressure drop across the reactor. Multiple injection of olefin may be used. The type of packing also influences the pressure drop due to the acid phase hold-up. The product mixture before fractionation is the preferred circulating solvent. The acid emulsion separates rapidly from the hydrocarbon liquid and is normally recycled with only a few minutes residence time in the bottom phase separator. Because the products are in essence rapidly extracted from the acid phase (emulsion), the reaction and/or emulsion promoters used in conventional sulfuric acid alkylation processes may be added without the usual concern for breaking the emulsion. The processes may be described as hydrocarbon-continuous as opposed to acid-continuous.

In some embodiments, the disperser may include a conventional liquid-liquid coalescer of a type which is operative for coalescing vaporized liquids. These are commonly known as "mist eliminators" or "demisters." However, dispersers used herein may function to disperse the fluid materials in the reactor for better contact. A suitable disperser may include a mesh such as a co-knit wire and fiberglass mesh. For example, it has been found that a 90 needle tubular co-knit mesh of wire and multifilament fiberglass, such as manufactured by Amistco Separation Products, Inc. of Alvin, Tex., may be effective; however, it will be understood that various other materials, such as co-knit wire and multi filament TEFLON (available from DuPont), steel wool, polypropylene, PVDF, polyester or various other co-knit materials may also be effectively used as a disperser. Various wire screen type packings may be used where the screens are woven rather than knitted. Other acceptable dispersers may include perforated sheets and expanded metals, open flow cross channel structures that are co-woven with fiberglass or other materials such as polymers co-knit with the wire mesh expanded or perforated sheets. Additionally the multi-filament component may be catalytic. The multi-filament catalytic material may be polymers, such as sulfonated vinyl resin (e.g., AMBERLYST) and catalytic metals such as Ni, Pt, Co, Mo, and Ag.

Other suitable dispersers may include structured catalytic distillation packings which are intended to hold particulate catalysts, or structured distillation packings composed of a catalytically active material, such as that disclosed in U.S. Pat. No. 5,730,843 which is incorporated herein in its entirety and which discloses structures that have a rigid frame made of two substantially vertical duplicate grids spaced apart and held rigid by a plurality of substantially horizontal rigid members and a plurality of substantially horizontal wire mesh tubes mounted to the grids to form a plurality of fluid pathways among the tubes, the tubes being empty or containing catalytic or non catalytic materials; and structured packings which are catalytically inert, such as those constructed of corrugated metal bent at various angles, crimped wire mesh, or grids which may be horizontally stacked one on top of the other, such as disclosed in U.S. Pat. No. 6,000,685, which is incorporated herein in its entirety and which discloses contact structures comprising a plurality of sheets of wire mesh formed into vee-shaped corrugations having flats between the vees, said plurality of sheets being of substantially uniform size having the peaks oriented in the same direction and substantially in alignment, said sheets being separated by a plurality of rigid members oriented normally to and said resting upon said vees.

Other suitable dispersers may include: (A) random or dumped distillation packings which are: catalytically inert dumped packings contain higher void fraction and maintain a relatively large surface area, such as, Berl Saddles (Ceramic), Raschig Rings (Ceramic), Raschig Rings (Steel), Pall rings (Metal), Pall rings (Plastic, e.g., polypropylene) and the like and catalytically active random packings which contain at least one catalytically active ingredient, such as Ag, Rh, Pd, Ni, Cr, Cu, Zn, Pt, Tu, Ru, Co, Ti, Au, Mo, V, and Fe as well as impregnated components such as metal-chelate complexes, acids such as phosphoric acid, or bonded, inorganic, powdered materials with catalytic activity; and (B) monoliths which are catalytically inert or active which are structures containing multiple, independent, vertical channels and may be constructed of various materials such as plastic, ceramic, or metals, in which the channels are typically square; however, other geometries may be used and may be coated with catalytic materials.

The dispersers may have at least 50 volume % open space in some embodiments, and up to about 97 volume % open space in other embodiments. Dispersers may be positioned within the reaction zone in the reactor. Thus, for example, the multi-filament component and the structural element, e.g., knit wire, should comprise about 3 volume % to about 50 volume % of the total disperser, the remainder being open space.

The hydrocarbon feedstock undergoing alkylation according to embodiments disclosed herein may be provided to the reaction zone in a continuous hydrocarbon phase containing effective amounts of olefinic and isoparaffinic starting materials which are sufficient for forming an alkylate product. The olefin to isoparaffin mole ratio in the total reactor feed should range from about 1:1.5 to about 1:30, and preferably from about 1:5 to about 1:15. Lower olefin to isoparaffin ratios may also be used. Having established a stable operation within these parameters, it is highly desirable to maintain the operating stoichiometric ratios of the olefinic and isoalkane reactants and thereby maintain the productivity of the alkylation unit at a constant level. The olefin component should preferably contain 2 to 16 carbon atoms and the isoparaffin component should preferably contain 4 to 12 carbon atoms.

Representative examples of suitable isoparaffins include isobutane, isopentane, 3-methylhexane, 2-methylhexane, 2,3-dimethylbutane and 2,4-dimethylbexane. Representative examples of suitable olefins include butene-2, isobutylene, butene-1, propylene, pentenes, ethylene, hexene, octene, and heptene, merely to name a few and as described above may be oligomers of these olefins.

In some embodiments, the alkylation processes described herein may contact relative amounts of acid and hydrocarbon fed to the top of the reactor in a volumetric ratio ranging from about 0.01:1 to about 2:1; in a ratio ranging from about 0.05:1 to about 1.5:1 in other embodiments; and in a ratio ranging from about 0.1:1 to about 1:1 in yet other embodiments.

In general, the particular operating conditions used in the alkylation processes described herein may depend to some degree upon the specific alkylation reaction being performed. Process conditions such as temperature, pressure and space velocity as well as the molar ratio of the reactants will affect the characteristics of the resulting alkylate product and may be adjusted in accordance with parameters known to those skilled in the art.

An advantage of operating at the boiling point of the present reaction system is that there is some evaporation which aids in dissipating the heat of reaction and making the temperature of the incoming materials closer to that of the materials leaving the reactor as in an isothermal reaction. Once the alkylation reaction has gone to completion, the reaction mixture is transferred to a suitable separation vessel where the hydrocarbon phase containing the alkylate product and any unreacted reactants is separated from the acid. The typical density for the hydrocarbon phase ranges from about 0.6 g/cc to about 0.8 g/cc and since densities for the acid generally fall within the ranges of about 0.9 g/cc to about 2.0 g/cc. The two phases are preferably separable by a conventional distillation, which provides a reusable isoalkane.

As described above, embodiments disclosed herein relate to processes for producing an alkylate having a low Reid vapor pressure. The processes may include contacting a $C_{6+}$-containing hydrocarbon stream comprising and a mixture of isopentane and isobutane in the presence of an acid catalyst in an alkylation reactor to form a dilute alkylate. The $C_{6+}$-containing hydrocarbon stream may include at least one of a) oligomers of $C_3$ to $C_5$ olefins, and b) a dilute alkylate of $C_3$ to $C_5$ olefins with at least one of $C_3$ to $C_5$ olefins, oligomers of $C_3$ to $C_5$ olefins. In some embodiments, the isoparaffin mixture may contain $C_4$, $C_5$, $C_6$, $C_7$, $C_8$, and heavier isoparaffins. Following alkylation, the isobutane and isopentane fractions may be recycled to the alkylation reactor, where the isopentane recycle may aid in controlling the formation or production of isopentane during the alkylation process. In this manner, the process may be a net consumer of pentane, resulting in a final product having a low Reid vapor pressure.

Feed Pretreatment

Olefin feed streams used herein may be hydrotreated to remove dienes prior to entering the alkylation process. The removal of butadienes and pentadienes is an important element in increasing catalyst life in the alkylation process. For processes that include reactive distillation for the oligomerization reactors to provide a purified oligomer product, the hydrotreatment step may be included in the catalytic distillation column used to produce the oligomer stream. For feeds to oligomerization reactors, the removal of basic compounds may be required to maintain catalyst life. For butylene containing streams, this may include the use of a water wash column for removal of nitriles.

As described above, embodiments disclosed herein relate to processes for producing an alkylate having a low Reid vapor pressure. The processes may include contacting a $C_{6+}$-containing hydrocarbon stream, isopentane, and isobutane in the presence of an acid catalyst in an alkylation reactor to form a dilute alkylate. In some embodiments, the $C_{6+}$-containing hydrocarbon stream may include oligomers of $C_3$ to $C_5$ olefins. In other embodiments, the $C_{6+}$-containing hydrocarbon stream may include a dilute alkylate of $C_3$ to $C_5$ isoparaffins with at least one of $C_3$ to $C_5$ olefins and oligomers of $C_3$ to $C_5$ olefins.

The resulting alkylate product may be fractionated to form an isobutane-rich fraction, a n-butane-rich fraction, a fraction comprising isopentane, and an alkylate product having a Reid vapor pressure less than 0.35 bar (5 psi); in other embodiments, the Reid vapor pressure may be less than 0.28 bar (4 psi); and less than 0.21 bar (3 psi) in yet other embodiments. The isobutane and isopentane fractions may be recycled to the alkylation reactor, where the isopentane recycle may aid in controlling the formation or production of isopentane during the alkylation process.

Figure 2:
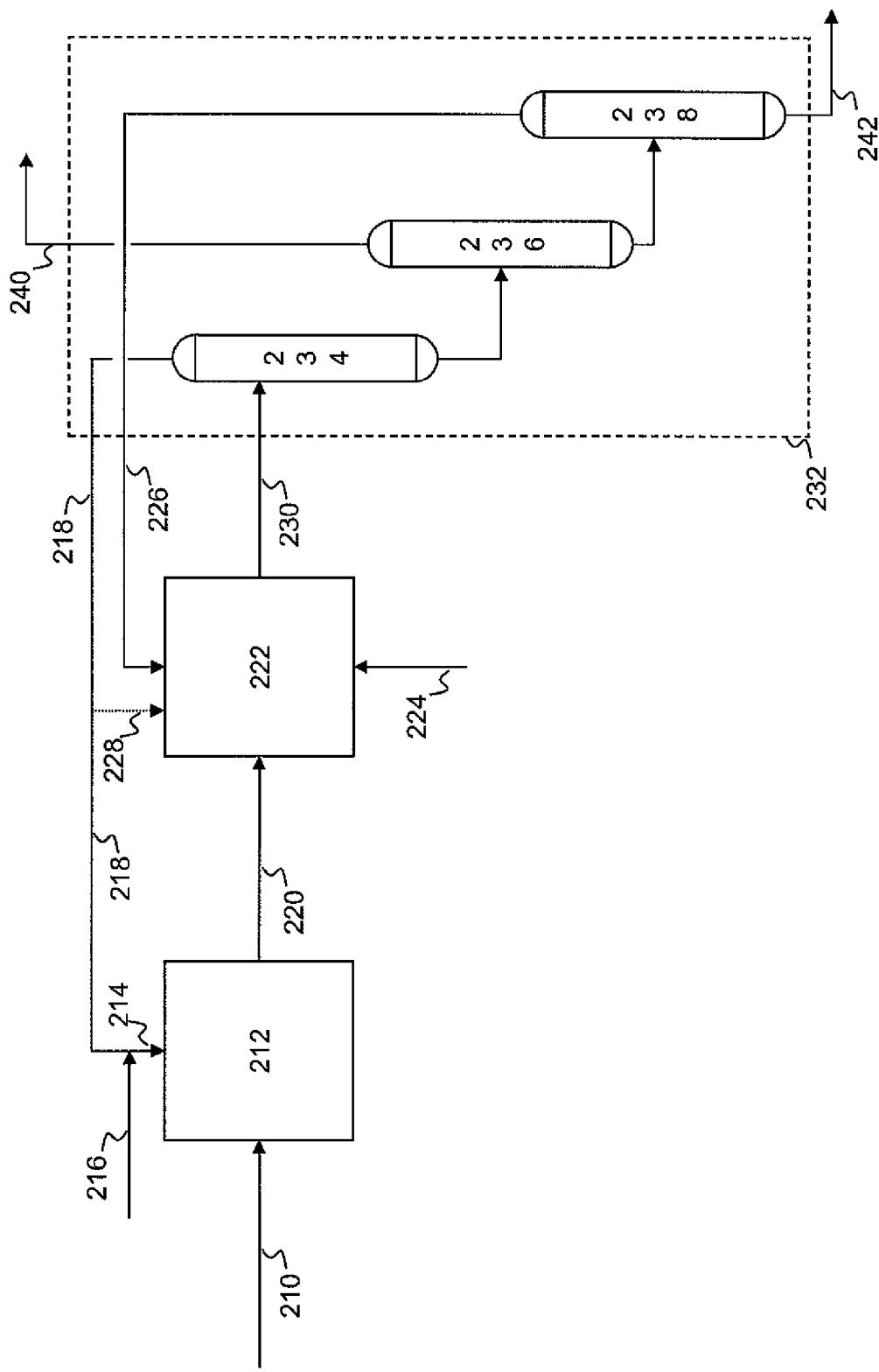
FIG. 2 is a simplified flow diagram of alkylation processes according to embodiments disclosed herein.
Figure 3:
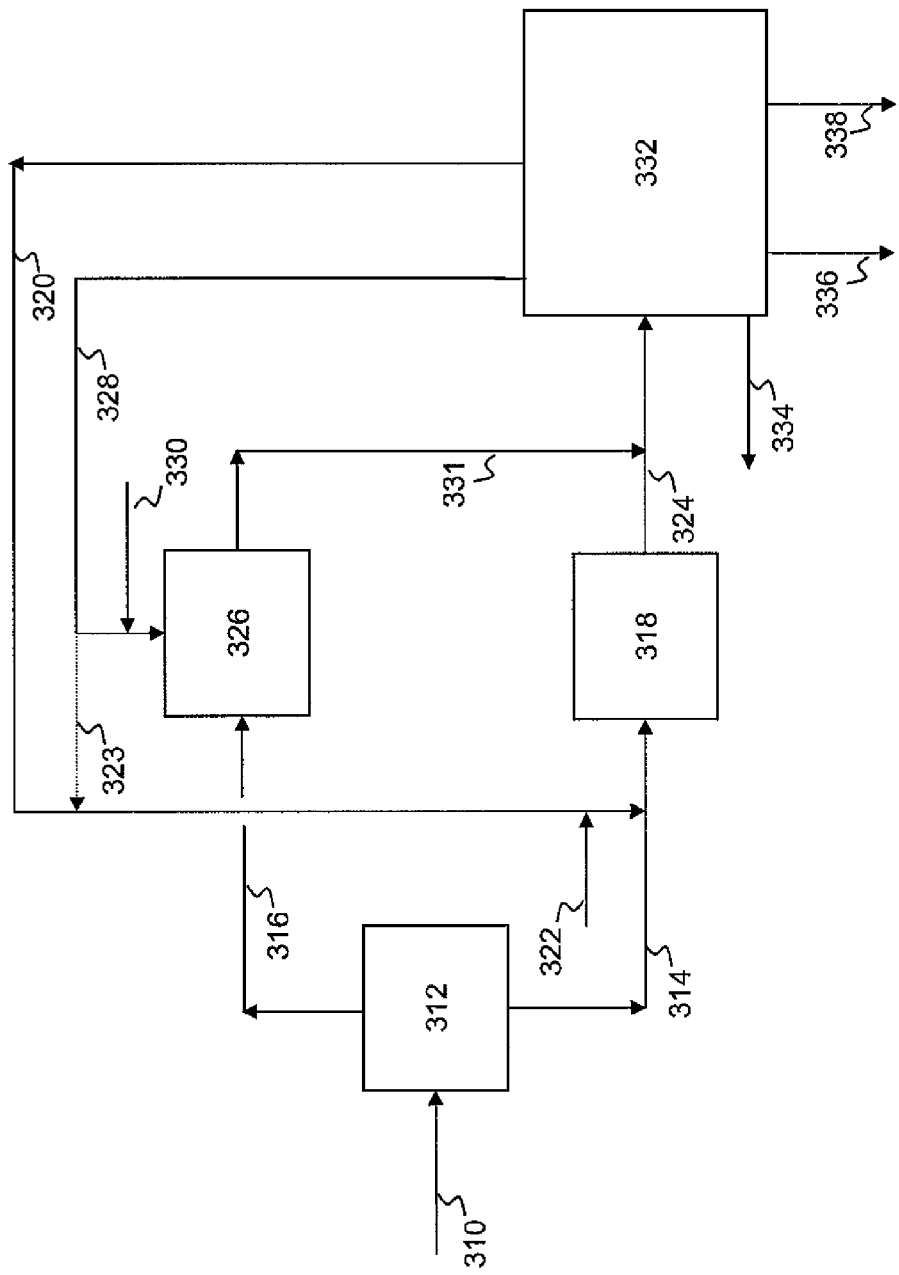
FIG. 3 is a simplified flow diagram of alkylation processes according to embodiments disclosed herein.

Embodiments of the above-described processes for alkylation with net pentane consumption are illustrated in FIGS. 1-3, each of which is a simplified flow diagram. Accordingly, items such as valves, reboilers, pumps, etc., have been omitted.

Referring now to FIG. 1, a process for alkylation according to embodiments disclosed herein is illustrated. Olefins or a mixture including olefins may be fed via flow line 10 to oligomerization reactor 12. Isobutane and/or isopentanes may be fed to oligomerization reactor 12 via line 14 to provide an additional heat sink to remove a portion of the heat of reaction generated during the oligomerization. The isobutane and isopentanes may include at least one of fresh isobutane feed 16 and recycle isobutane and isopentane feeds 18, 20, respectively, including isobutane and isopentanes recovered downstream of the oligomerization reactor 12, as will be discussed below. The effluent 22 from the oligomerization reactor is fed to alkylation unit 24 where substantially all of the olefins and olefin oligomers are reacted with isobutane to produce alkylate.

Make-up isobutane and/or make-up isopentanes may be added as needed via flow lines 26, 28, respectively. If the olefins in feed line 22 are higher stoichiometrically than the isobutane and isopentanes, make up isobutane and isopentanes may be added via flow lines 26, 28. The effluent from the alkylation unit in flow line 30 may be fed to fractionation unit 32, which may include one or more of a depropanizer, debutanizer, deisobutanizer, deisopentanizer, which may be operated in series or in parallel, with or without side draws to recover various products as known in the art. The fractionation unit may be used to recover various products and reactants, including isobutane, which may be recycled via flow line 18, isopentanes, which may be recycled via flow line 20, and normal butane, which may be recovered via flow line 34. Following the selected fractionation scheme, the resulting low Reid pressure alkylate product may be removed from the fractionation unit via flow line 36.

Referring now to FIG. 2, a process for alkylation, according to other embodiments disclosed herein, is illustrated. Olefins, olefin oligomers, or a mixture including olefins or olefin oligomers may be fed via flow line 210 to first alkylation unit 212. A desired amount of isobutane may be fed to first alkylation unit 212 via line 214 to maintain the desired stoichiometric ratio of olefins and isobutane in the feed to the first alkylation unit 212. In alkylation unit 212, at least a portion of the olefins and olefin oligomers may be reacted with isobutane to produce alkylate. The isobutane may include at least one of fresh isobutane feed 216 and recycle isobutane feed 218, including isobutane recovered downstream of the first alkylation unit 212, as will be discussed below.

The dilute alkylate effluent 220 from the first alkylation unit 212 may be fed to second alkylation unit 222. Fresh olefins or olefin oligomers may be fed to second alkylation unit 222 via flow line 224. Additionally, isopentanes may be recycled to second alkylation unit 222 via flow line 226. If necessary to maintain a desired ratio of olefin to isoparaffin, additional isoolefins, such as recycle isobutane, may be fed to second alkylation unit via flow line 228. In some embodiments, fresh isoparaffin (not shown) may also be fed to second alkylation unit 222 to maintain a desired ratio of olefin to isoparaffin. In second alkylation unit 222, substantially all of the remaining olefins and olefin oligomers (i.e., those not reacted in the first alkylation unit 212) and any fresh olefins or olefin oligomers fed via flow line 224 may be reacted with isobutane and isopentane to produce alkylate.

The effluent from second alkylation unit 222 in flow line 230 may be fed to fractionation unit 232, which may include one or more of a depropanizer, debutanizer, deisobutanizer, deisopentanizer, which may be operated in series or in parallel, with or without side draws to recover various products as known in the art. If necessary, in some embodiments it may be preferable to associate a depropanizer with a refrigeration section included with the alkylation unit. As illustrated, fractionation unit 232 includes a deisobutanizer 234, debutanizer 236, and a deisopentanizer 238 operated in series, and may be used to recover isobutane via flow line 218, which may be recycled as discussed above, isopentanes via flow line 226, which also may be recycled as discussed above, and normal butane via flow line 240. Following the selected fractionation scheme, the resulting low Reid pressure alkylate product may be removed from the fractionation unit via flow line 242.

Referring now to FIG. 3, another process for alkylation, according to embodiments disclosed herein, is illustrated. Olefins or a mixture including olefins may be fed via flow line 310 to oligomerization unit 312. In some embodiments, oligomerization unit 312 may include an oligomerization reactor, such as a fixed bed, trickle bed, or boiling point reactor, as described above, and a separator for separating the resulting oligomers from light, unreacted olefins. In other embodiments, oligomerization unit 312 may include a catalytic distillation column for concurrently oligomerizing and separating oligomers from the light, unreacted olefins. Heavy olefins may be recovered via flow line 314, and light olefins may be recovered via flow line 316.

Olefin oligomers in flow line 314 may be fed to first alkylation unit 318. A desired amount of isopentanes may be added as needed via flow line 320, which may include isopentane recycled from downstream of the first alkylation unit 318, as will be discussed below. If the olefin oligomers in feed line 314 are higher stoichiometrically than the isopentanes recycled, make-up isobutane or isopentane may be added via flow line 322, or may include recycle isobutane added via flow line 323. In first alkylation unit 318, substantially all of the olefin oligomers may be reacted with isobutane to produce a first dilute alkylate, which may be recovered via flow line 324.

Light olefins in flow line 316 may be fed to second alkylation unit 326. A desired amount of isobutane may be added as needed via flow line 328, which may include isobutane recycled from downstream of the second alkylation unit 326, as will be discussed below. If the light olefins in feed line 316 are higher stoichiometrically than the isobutane recycled, make up isobutane may be added via flow line 330. In second alkylation unit 326, substantially all of the light olefins may be reacted with isobutane to produce a second dilute alkylate, which may be recovered via flow line 331.

The effluents from the alkylation units in flow lines 324, 331 may be separately or collectively fed to fractionation unit 332, which may include one or more of a depropanizer, debutanizer, deisobutanizer, deisopentanizer, which may be operated in series or in parallel, with or without side draws to recover various products as known in the art. The fractionation unit may be used to recover various products and reactants, including isobutane, which may be recycled via flow line 328, isopentanes, which may be recycled via flow line 320, propane, which may be recovered via flow line 334, and normal butane, which may be recovered via flow line 336. Following the selected fractionation scheme, the resulting low Reid pressure alkylate product may be recovered from the fractionation unit via flow line 338.

EXAMPLE

Oligomerization and alkylation with isoparaffin recycle is performed as in the embodiment illustrated in FIG. 1. Isobutane and isopentane recycle is combined with the olefin feed in the oligomerization unit. In this particular case, the olefin feed and makeup isobutane fed to the overall process system contain only minor amounts of $C_{5+}$ material. The RVP for the process is controlled using internal isopentane recycle through fractionation section 32. The isopentane being recycled is considered unrelated to that coming in with the overall process feed streams; the isopentane is produced as a side-product during the alkylation of $C_4$ olefins primarily with isobutane. The quantity of isopentane in the alkylate product (stream 36) is a result of the relative amount of isopentane recycle utilized within the process. The product RVP is controlled using the fractionation section, and the ability to recycle produced isopentane back to the alkylation section for subsequent reaction of isopentane with the $C_4$ olefin feed. This reaction is less pronounced at the higher ratios of isopentane to total isoparaffins used as compared to that of the reaction between isobutane and $C_4$ olefins. In the fractionation section, it is recognized that in order to recycle a large quantity of isopentane, the isopentane fraction may contain small amounts of $C_{6+}$ isoparaffins.

In the pilot operation, the light olefin stream sent to the process (stream 10) is composed, by weight, of approximately half isobutene and half isobutane. A recycle stream from a fractionation system, primarily isobutane and isopentane along with a small quantity of n-butane (stream 18), is mixed with the olefin feed and is introduced into an oligomerization unit. In the oligomerization unit, the isobutene is converted (>99% conversion) into isobutene oligomers using an acid resin catalyst. The oligomers along with additional isobutane or isopentane, if needed (streams 26 and 28 respectively), are then introduced into the alkylation unit, which is controlled at an operating temperature between −5 to −1° C. (between 23 and 30° F.). The quantity of isobutane and isopentane in the net feed to the alkylation unit (24) is run in considerable mass excess relative to the total quantity of oligomers being fed. The [isobutane+isopentane] to [oligomer & olefin] ratio (the I:O ratio) is held at 4 and higher in the net feed to both the oligomerization unit and the alkylation unit. Isoparaffin recycle from the fractionation section is utilized in the oligomerization section to deal with the exothermic heat release within the reactor. Reaction between the alkylation feed oligomers/olefins and the isoparaffins (isobutane and isopentane) produces a dilute alkylate stream which is sent to fractionation (32).

As indicated, a portion of the alkylate product includes an isopentane component. The quantity of isopentane present in the final alkylate product recovered is controlled using fractionation section 32, via control of the isopentane recycled back to the oligomerization unit or directly to the alkylation unit 24 via stream 28. The isopentane, not recovered with the alkylate product (stream 36) is recycled along with isobutane, increasing the production of heavier $C_9$ alkylate components within the alkylation unit. This provides the means to lower the overall vapor pressure in the product (Stream 36). Alkylate in the gasoline boiling range with RVP of between 0.15 and 0.35 bar (2.2 and 5 psi) is produced at alkylate product rates of between 2-3 BBL/day (about 0.3 to 0.5 m$^3$/day) using a 7.6 cm (3 inch) diameter pilot scale unit. Non-condensable light ends contained in the overall process feed streams are vented through the compression section of the alkylation unit in order to maintain the desired compressor discharge pressure and alkylation reactor discharge pressure/temperature.

Several conditions are demonstrated in the 7.6 cm (3 inch) pilot scale unit to show how RVP control utilizing a feed olefin stream, containing an oligomer component, can produce a low vapor pressure alkylate product. The primary condition provided during the testing is the production of alkylate using oligomers primarily formed from isobutene. This condition is demonstrated whereby isopentane recycle is provided to adjust the product RVP from approximately 0.35 bar (5 psia) to 0.18 bar (2.6 psia), by adjusting the quantity of isopentane recycle. In this operation, a deisopentanizer column is utilized for the recycle of isopentane from fractionation. Operational description of the oligomer operation, isoparaffin recycle rates and ratios, associated alkylation unit operation, and the resulting product are provided in Table 1.

TABLE 1

| Condition | Base | Low RVP |
|---|---|---|
| Oligomerization | | |
| LHSV (l/h) | 11 | 11.5 |
| Pressure, bar (psig) | 6.9 (100) | 6.9 (100) |
| % Isobutene conversion | 99.8 | 99.9 |
| Alkylation | | |
| OSV (l/h) | 0.45 | 0.47 |
| Average Reactor Bed Temperature, | −4 (24) | −4 (24) |
| ° C. (° F.) | | |
| I:O Ratio (mass) | 6 | 6 |
| Isopentane/total isoparaffin from fractionation | 0 | 0.08 |
| Product | | |
| RVP, bar (psia) | 0.31 (4.43) | 0.18 (2.64) |
| T10, ° C. (° F.) | 86 (187) | 93 (200) |
| T50, ° C. (° F.) | 112 (235) | 113 (236) |
| T90, ° C. (° F.) | 193 (379) | 183 (361) |
| Road Octane Number (RON) | 93.6 | 92.7 |

During this pilot run, the oligomerization reactor is packed with an acid resin catalyst and run under boiling point conditions, whereby the effluent on the outlet of the reactor is two-phase flow. Isobutene conversion within the oligomerization reactor is >99% conversion. In the alkylation unit, OSV is the olefin space velocity, (e.g., ft$^3$/hr $C_4$ olefin equivalent volume to ft$^3$ of acid in a packed reactor (also run in Boiling Point Mode)). The alkylation temperature is set by adjusting the alkylation unit suction pressure on the refrigeration compressor, and isopentane is recycled by fractionating a portion of isopentane overhead in the deisopentanizer unit. Table 1 shows two conditions, with and without isopentane recycle. The unit operation is able to vary the product RVP approximately 0.14 bar (2 psia), via increasing the amount of isopentane in the isoparaffin recycle to 8% of the total isoparaffins set to the alkylation unit. The associated octane of the product is shown to decrease, as now the alkylate production is geared more toward increased alkylation of isopentane rather than isobutane and thus higher production of $C_9$ components verses the (higher octane) $C_8$ trimethylpentane components.

Advantageously, embodiments disclosed herein may provide for production of a low Reid vapor pressure alkylate product. Additionally, embodiments disclosed herein may provide for the recycle of isopentane within the process scheme, resulting in the net consumption of pentanes. The resulting alkylate products, having a low Reid vapor pressure, may be readily blended with ethanol due to the lower concentration of $C_5$'s in the resulting alkylate.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for producing an alkylate having a low Reid vapor pressure, the process comprising:
   contacting a $C_{6+}$-containing hydrocarbon stream, wherein the $C_{6+}$-containing hydrocarbon stream comprises at least one of oligomers of $C_3$ to $C_5$ olefins and a first dilute alkylate produced by contacting an isoparaffin with at least one of $C_3$ to $C_5$ olefins and oligomers of $C_3$ to $C_5$ olefins, with a mixture of isopentane and isobutane in the presence of an acid catalyst in an alkylation reactor to form a second dilute alkylate product;
   fractionating the second dilute alkylate product to form an isobutane-rich fraction, a n-butane-rich fraction, a fraction comprising isopentane, and an alkylate product having a Reid vapor pressure less than 0.35 bar (5 psi);
   recycling at least a portion of the fraction comprising isopentane to the alkylation reactor.

2. The process of claim 1, wherein the alkylate product has a Reid vapor pressure of less than 0.21 bar (3 psi).

3. The process of claim 1, further comprising oligomerizing $C_3$ to $C_5$ olefins to form the oligomers of $C_3$ to $C_5$ olefins.

4. The process of claim 3, further comprising recycling one of at least a portion of the isobutane rich fraction and at least a portion of the isopentane fraction to the oligomerizing.

5. The process of claim 3, further comprising fractionating the oligomers of $C_3$ to $C_5$ olefins from unreacted olefins.

6. The process of claim 5, wherein the oligomerizing and the fractionating occur concurrently in a distillation column reactor.

7. The process of claim 5, further comprising:
contacting the unreacted olefins with at least one of isopentane and isobutane in the presence of an acid catalyst in a second alkylation reactor to form a second dilute alkylate product; and
fractionating the second dilute alkylate product with the dilute alkylate product.

8. The process of claim 7, further comprising recycling at least a portion of one of the isobutane rich fraction and at least a portion of the isopentane fraction to the second alkylation reactor.

9. The process of claim 1, further comprising contacting $C_3$ to $C_5$ olefins with at least one of isobutane and isopentane to form the dilute alkylate of $C_3$ to $C_5$ olefins.

10. The process of claim 1, further comprising recycling at least a portion of the isobutane-rich fraction to alkylation reactor.

11. A process for producing an alkylate having a relatively low Reid vapor pressure, the process comprising:
contacting a first hydrocarbon stream comprising at least one of $C_3$ to $C_5$ olefins and oligomers of $C_3$ to $C_5$ olefins with isobutane in the presence of an acid catalyst in a first alkylation reactor to form a dilute alkylate of $C_3$ to $C_5$ olefins;
contacting the dilute alkylate of $C_3$ to $C_5$ olefins and a second hydrocarbon stream comprising at least one of $C_3$ to $C_5$ olefins and oligomers of $C_3$ to $C_5$ olefins with isopentane in a second alkylation reactor to form a second dilute alkylate of $C_3$ to $C_5$ olefins;
fractionating the second dilute alkylate to form an isobutane-rich fraction, a n-butane-rich fraction, a fraction comprising isopentane, and an alkylate product having a Reid vapor pressure less than 0.35 bar (5 psi);
recycling at least a portion of the fraction comprising isopentane to the second alkylation reactor; and
recycling at least a portion of the isobutane-rich fraction to the first alkylation reactor.

12. The process of claim 11, wherein the alkylate product has a Reid vapor pressure of less than 0.21 bar (3 psi).

13. The process of claim 11, further comprising recycling at least a portion of the isobutane-rich fraction to the second alkylation reactor.

14. The process of claim 11, further comprising recycling at least a portion of the fraction comprising isopentane to the first alkylation reactor.

15. The process of claim 11, wherein the fractionating further comprises recovering a $C_3$ fraction.

16. A process for producing an alkylate having a relatively low Reid vapor pressure, the process comprising:
oligomerizing $C_3$ to $C_5$ olefins to form oligomers of $C_3$ to $C_5$ olefins;
contacting the oligomers of $C_3$ to $C_5$ olefins with a mixture of isopentane and isobutane in the presence of an acid catalyst in an alkylation reactor to form a dilute alkylate;
fractionating the dilute alkylate to form an isobutane-rich fraction, a n-butane-rich fraction, a fraction comprising isopentane, and an alkylate product having a Reid vapor pressure less than 0.35 bar (5 psi);
recycling at least a portion of the fraction comprising isopentane to the alkylation reactor.

17. The process of claim 16, wherein the alkylate product has a Reid vapor pressure of less than 0.21 bar (3 psi).

18. The process of claim 16, further comprising fractionating the oligomers to form a light olefin fraction and a fraction comprising the $C_3$ to $C_5$ oligomers.

19. The process of claim 18, further comprising:
contacting the light olefin fraction with at least one of isopentane and isobutane in the presence of an acid catalyst in a second alkylation reactor to form a second dilute alkylate.

20. The process of claim 19, further comprising:
contacting the unreacted olefins with at least one of isopentane and isobutane in the presence of an acid catalyst to form a second dilute alkylate; and
fractionating the second dilute alkylate with the dilute alkylate.

21. The process of claim 19, further comprising recycling a portion of at least one of the isobutane-rich fraction and the isopentane fraction to the second alkylation reactor.

* * * * *